United States Patent
Abbitt et al.

(10) Patent No.: US 11,236,348 B2
(45) Date of Patent: Feb. 1, 2022

(54) TRANSCRIPTIONAL TERMINATORS FOR GENE EXPRESSION IN PLANTS

(71) Applicant: PIONEER HI-BRED INTERNATIONAL, INC., Johnston, IA (US)

(72) Inventors: Shane E. Abbitt, Ankeny, IA (US); Karri Klein, Des Moines, IA (US); David Selinger, Hockessin, DE (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/346,411

(22) PCT Filed: Nov. 15, 2017

(86) PCT No.: PCT/US2017/061748
§ 371 (c)(1),
(2) Date: Apr. 30, 2019

(87) PCT Pub. No.: WO2018/102131
PCT Pub. Date: Jun. 7, 2018

(65) Prior Publication Data
US 2020/0063149 A1    Feb. 27, 2020

Related U.S. Application Data

(60) Provisional application No. 62/579,253, filed on Oct. 31, 2017, provisional application No. 62/427,491, filed on Nov. 29, 2016.

(51) Int. Cl.
*C12N 15/82* (2006.01)

(52) U.S. Cl.
CPC ..... *C12N 15/8216* (2013.01); *C12N 15/8213* (2013.01); *C12N 2310/20* (2017.05); *C12N 2800/30* (2013.01); *C12N 2800/70* (2013.01); *C12N 2800/80* (2013.01)

(58) Field of Classification Search
None
See application file for complete search history.

(56) References Cited

U.S. PATENT DOCUMENTS

| 2017/0121722 A1* | 5/2017 | Anand | C07K 14/415 |
| 2018/0119162 A1* | 5/2018 | Elsing | A01H 1/04 |

FOREIGN PATENT DOCUMENTS

| WO | 1996/029858 A1 | 10/1996 |
| WO | 2013/012729 A2 | 1/2013 |
| WO | 2013/019461 A1 | 2/2013 |
| WO | 2014/126755 A1 | 8/2014 |
| WO | 2016/149352 A1 | 9/2016 |

OTHER PUBLICATIONS

Kuroda et al, 2010, Bioscience, Biotechnology, and Biochemistry, 74:2348-2351.*
Lau et al, 2009, Biotechnology Advances, 27:1015-1022.*
Collonnier et al, 2017, Methods, 121-122:103-117.*
Liu, Xiaochuan, et al.: "LSD: a leaf senescence database", Nucleic Acids Research, Jan. 1, 2011 (Jan. 1, 2011), vol. 39.
Wu, Xiao-Yuan, et al.: "Transcriptome profiling of developmental leaf senescence in sorghum (Sorghum bicolor)", Plant Molecular Biology, Jan. 1, 2011 (Jan. 1, 2011), vol. 92, No. 4, pp. 555-580.
Database Geneseq: XP002777017, Nov. 17, 2016 (Nov. 17, 2016).
International Search Report and Written Opinion, International Application No. PCT/US2017/061748 dated Mar. 20, 2018.

* cited by examiner

*Primary Examiner* — Jason Deveau Rosen (57) ABSTRACT

The present disclosure discloses polynucleotide sequences that can be used to regulate gene expression in plants. Terminator sequences from *Sorghum bicolor* and *Oryza sativa* that are functional in plants are disclosed. Nucleic acid molecules, recombinant expression constructs, plants and seed comprising these terminator sequences are further disclosed.

22 Claims, 1 Drawing Sheet
Specification includes a Sequence Listing.

TRANSCRIPTIONAL TERMINATORS FOR GENE EXPRESSION IN PLANTS

REFERENCE TO SEQUENCE LISTING SUBMITTED ELECTRONICALLY

The official copy of the sequence listing is submitted electronically via EFS-Web as an ASCII formatted sequence listing with a file named "7166USPCT_Sequence_Listing" created on Apr. 22, 2019, and having a size of 14.8 kilobytes and is filed concurrently with the specification. The sequence listing contained in this ASCII formatted document is part of the specification and is herein incorporated by reference in its entirety.

FIELD OF DISCLOSURE

The present disclosure relates to the field of plant molecular biology and plant genetic engineering. More specifically, it relates to novel plant terminator sequences and their use to regulate gene expression in plants.

BACKGROUND

Recent advances in plant genetic engineering have opened new doors to engineer plants to have improved characteristics or traits. These transgenic plants characteristically have recombinant DNA constructs in their genome that have protein coding region operably linked to multiple regulatory regions that allow accurate expression of the transgene. A few examples of regulatory elements that help regulate gene expression in transgenic plants are promoters, introns, terminators, enhancers and silencers.

Plant genetic engineering has advanced to introducing multiple traits into commercially important plants, also known as gene stacking. This is accomplished by multigene transformation, where multiple genes are transferred to create a transgenic plant that might express a complex phenotype, or multiple phenotypes. But it is important to modulate or control the expression of each transgene optimally. The regulatory elements need to be diverse, to avoid introducing into the same transgenic plant repetitive sequences, which has been correlated with undesirable negative effects on transgene expression and stability (Peremarti et al. (2010) *Plant Mol Biol* 73:363-378; Mette et al. (1999) EMBO J 18:241-248; Mette et al. (2000) EMBO J 19:5194-5201; Mourrain et al. (2007) Planta 225:365-379, U.S. Pat. Nos. 7,632,982, 7,491,813, 7,674,950, PCT Application No. PCT/US2009/046968). Therefore, it is important to discover and characterize novel regulatory elements that can be used to express heterologous nucleic acids in important crop species. Diverse regulatory regions can be used to control the expression of each transgene optimally.

Regulatory sequences located downstream of coding regions contain signals required for transcription termination and 3' mRNA processing, and are called terminator sequences. The terminator sequences play a key role in mRNA processing, localization, stability and translation (Proudfoot, N. (2004) *Curr. Op. Cell Biol* 16:272-278; Gilmartin, 2005).

SUMMARY

Regulatory sequences for modulating gene expression in plants are disclosed. Specifically, the present disclosure relates to terminator sequences. Recombinant DNA constructs comprising terminator sequences are provided.

An embodiment of this disclosure is an isolated polynucleotide sequence comprising: (a) the sequence set forth in any of SEQ ID NOS:1-7 or 24; (b) a sequence with at least 95% sequence identity to any of SEQ ID NOS:1-7 or 24; or (c) a sequence comprising a fragment of (a) or (b), wherein the isolated polynucleotide sequence functions as a terminator in a plant cell and is operably linked to a heterologous polynucleotide sequence. Another embodiment of this disclosure is a recombinant construct comprising an isolated polynucleotide sequence comprising: (a) the sequence set forth in any of SEQ ID NOS:1-7 or 24; (b) a sequence with at least 95% sequence identity to any of SEQ ID NOS:1-7 or 24; or (c) a sequence comprising a functional fragment of (a) or (b), wherein the isolated polynucleotide sequence functions as a terminator in a plant cell and operably linked to a heterologous nucleotide sequence. This recombinant construct may further comprise a promoter and a heterologous polynucleotide, wherein the promoter and the heterologous polynucleotide are operably linked to the isolated polynucleotide sequence.

Another embodiment of this disclosure is a method of expressing a heterologous polynucleotide in a plant, comprising the steps of (a) introducing into a regenerable plant cell the recombinant DNA construct described above; (b) regenerating a transgenic plant from the regenerable plant cell of (a); and (c) obtaining a progeny plant from the transgenic plant of step (b), wherein the transgenic plant and the progeny plant comprises the recombinant DNA construct and exhibits expression of the heterologous polynucleotide.

In a fourth embodiment, this disclosure concerns a vector, cell, plant, or seed comprising a recombinant DNA construct comprising the terminator sequences described in the present disclosure.

The disclosure encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the terminator sequences described in the present disclosure is a monocotyledonous plant. In another embodiment, the plant comprising the terminator sequences described in the present disclosure is a maize plant.

BRIEF DESCRIPTION OF DRAWINGS AND SEQUENCE LISTING

The disclosure can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

Various sequences are referenced in the disclosure. Sequence identifiers are found below in Table 1.

TABLE 1

| SEQUENCE ID NUMBER | ORGANISM | IDENTITY |
|---|---|---|
| SEQ ID NO: 1 | Sorghum bicolor | SB-SAG12_TERM |
| SEQ ID NO: 2 | Sorghum bicolor | SB-CPI8_TERM |
| SEQ ID NO: 3 | Oryza sativa | OS-UBI_TERM |
| SEQ ID NO: 4 | Sorghum bicolor | SB-PMSP_TERM |
| SEQ ID NO: 5 | Sorghum bicolor | SB-CP1_TERM |
| SEQ ID NO: 6 | Sorghum bicolor | SB-SCI-1B_TERM |
| SEQ ID NO: 7 | Sorghum bicolor | SB-PEPC1_TERM |
| SEQ ID NO: 8 | Artificial seq - forward primer | SB-SAG12_TERM |
| SEQ ID NO: 9 | Artificial seq - reverse primer | SB-SAG12_TERM |
| SEQ ID NO: 10 | Artificial seq - forward primer | SB-CPI8_TERM |
| SEQ ID NO: 11 | Artificial seq - reverse primer | SB-CPI8_TERM |
| SEQ ID NO: 12 | Artificial seq - forward primer | OS-UBI_TERM |
| SEQ ID NO: 13 | Artificial seq - reverse primer | OS-UBI_TERM |
| SEQ ID NO: 14 | Artificial seq - forward primer | SB-PMSP_TERM |
| SEQ ID NO: 15 | Artificial seq - reverse primer | SB-PMSP_TERM |
| SEQ ID NO: 16 | Artificial seq - forward primer | SB-CP1_TERM |
| SEQ ID NO: 17 | Artificial seq - reverse primer | SB-CP1_TERM |
| SEQ ID NO: 18 | Artificial seq - forward primer | SB-SCI-1B_TERM |
| SEQ ID NO: 19 | Artificial seq - reverse primer | SB-SCI-1B_TERM |
| SEQ ID NO: 20 | Artificial seq - forward primer | SB-PEPC1_TERM |
| SEQ ID NO: 21 | Artificial seq - reverse primer | SB-PEPC1_TERM |
| SEQ ID NO: 22 | Solanum tuberosum | PINII control terminator |
| SEQ ID NO: 23 | Sorghum bicolor | SB-GKAF control terminator |
| SEQ ID NO: 24 | Sorghum bicolor | SB-PEPC1_TERM (MOD1) |

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"Transcription terminator", "termination sequences", or "terminator" refer to polynucleotide sequences located downstream of a coding sequence, including polyadenylation recognition sequences and other sequences encoding regulatory signals capable of affecting mRNA processing or gene expression, including for example stopping the transcriptional activity. The polyadenylation signal is usually characterized by affecting the addition of polyadenylic acid tracts to the 3' end of the mRNA precursor. A polynucleotide sequence with "terminator activity" refers to a polynucleotide sequence that, when operably linked to the 3' end of a second polynucleotide sequence that is to be expressed, is capable of terminating transcription from the second polynucleotide sequence. Transcription termination is the process by which RNA synthesis by RNA polymerase is stopped and both the RNA and the enzyme are released from the DNA template.

Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117).

As used herein, "SB terminator" or "OS terminator" refers to a nucleotide sequence from the *Sorghum bicolor* or *Oryza sativa* genomic sequences that functions as a terminator. The terminator can be the full-length terminator which comprises a sequence encoding the 3' untranslated region (3' UTR) of the gene and sequence downstream from the 3' UTR. The terminator can also be any functional fragment of SEQ ID NOS:1-7 or 24, including but not limited to SEQ ID NOS: 1-7 or 24, or a derivative of SEQ ID NOS: 1-7 or 24 obtained by deletion, substitution or addition of one or more nucleotides, wherein the fragment demonstrates terminator activity.

The 3' UTR sizes of the terminators of SEQ ID NOS: 1-7 and 24 are given in Table 2.

TABLE 2

| SEQ ID | TERM | TERM size | Native transcript ID | 3' UTR size |
| --- | --- | --- | --- | --- |
| 1 | SB-SAG12_TERM | 980 | Sobic.006G242000.1 | 445 |
| 2 | SB-CPI8_TERM | 980 | Sobic.001G324700.1 | 321 |
| 3 | OS-UBI_TERM | 950 | LOC_Os06g46770.1 | 385 |
| 4 | SB-PMSP_TERM | 964 | Sobic.010G250400.1 | 398 |
| 5 | SB-CP1_TERM | 989 | Sobic.004G142800.1 | 405 |
| 6 | SB-SCI-1B_TERM | 953 | Sobic.009G043400.1 | 381 |
| 7 | SB-PEPC1_TERM | 997 | Sobic.004G106900.1 | 271 |
| 24 | SB-PEPC1_TERM (MOD1) | 997 | Sobic.004G106900.1 | 271 |

The present disclosure encompasses functional fragments and variants of the terminator sequences disclosed herein.

A "functional fragment" of the terminator is defined as any subset of contiguous nucleotides of the terminator sequence disclosed herein, that can perform the same, or substantially similar function as the full-length terminator sequence disclosed herein. A "functional fragment" with substantially similar function to the full-length terminator disclosed herein refers to a functional fragment that retains the ability to terminate transcription largely at the same level as the full-length terminator sequence. A recombinant construct comprising a heterologous polynucleotide operably linked to a "functional fragment" of the terminator sequence disclosed herein exhibits levels of heterologous polynucleotide expression substantially similar to a corresponding recombinant construct comprising a heterologous polynucleotide operably linked to the full-length terminator sequence. A functional fragment can vary in size from about 50 to about 100; from about 100 to about 500 contiguous nucleotides.

A "variant", as used herein, is the sequence of the terminator or the sequence of a functional fragment of a terminator containing changes in which one or more nucleotides of the original sequence is deleted, added, and/or substituted, while substantially maintaining terminator function. One or more base pairs can be inserted, deleted, or substituted internally to a terminator, without affecting its activity. Fragments and variants can be obtained via methods such as site-directed mutagenesis and synthetic construction.

These terminator functional fragments will comprise at least about 20 contiguous nucleotides, preferably at least about 50 contiguous nucleotides, more preferably at least about 75 contiguous nucleotides, even more preferably at least about 100 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present disclosure.

The terms "substantially similar" and "corresponding substantially" as used herein refer to nucleic acid fragments, particularly terminator sequences, wherein changes in one or more nucleotide bases do not substantially alter the ability of the terminator to terminate transcription. These terms also refer to modifications, including deletions and variants, of the nucleic acid sequences of the instant disclosure by way of deletion or insertion of one or more nucleotides that do not substantially alter the functional properties of the resulting terminator relative to the initial, unmodified terminator. It is therefore understood, as those skilled in the art will appreciate, that the disclosure encompasses more than the specific exemplary sequences.

As will be evident to one of skill in the art, any heterologous polynucleotide of interest can be operably linked to the terminator sequences described in the current disclosure. Examples of polynucleotides of interest that can be operably linked to the terminator sequences described in this disclosure include, but are not limited to, polynucleotides comprising regulatory elements such as introns, enhancers, promoters, translation leader sequences, protein coding regions such as disease and insect resistance genes, genes conferring nutritional value, genes conferring yield and heterosis increase, genes that confer male and/or female sterility, antifungal, antibacterial or antiviral genes, and the like.

Likewise, the terminator sequences described in the current disclosure can be used to terminate transcription of any nucleic acid that controls gene expression. Examples of nucleic acids that could be used to control gene expression include, but are not limited to, antisense oligonucleotides, suppression DNA constructs, or nucleic acids encoding transcription factors.

Regulatory Sequences:

A recombinant DNA construct (including a suppression DNA construct) of the present disclosure may comprise at least one regulatory sequence. In an embodiment of the present disclosure, the regulatory sequences disclosed herein can be operably linked to any other regulatory sequence.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

The terms "real-time PCR", "quantitative PCR", "quantitative real-time PCR" and "QPCR" are used interchangeably herein, and represent a variation of the standard polymerase chain reaction (PCR) technique used to quantify DNA or RNA in a sample. Using sequence-specific primers and a probe, the relative number or copies of a particular DNA or RNA sequence are determined. The term relative is used since this technique compares relative copy numbers between different genes with respect to a specific reference gene. The quantification arises by measuring the amount of amplified product at each cycle during the PCR process. Quantification of amplified product is obtained using fluorescent hydrolysis probes that measure increasing fluorescence for each subsequent PCR cycle. The Ct (cycle threshold) is defined as the number of cycles required for the fluorescent signal to cross the threshold (i.e., exceeds background level). DNA/RNA from genes with higher copy numbers will appear after fewer PCR cycles; so, the lower a Ct value, the more copies are present in the specific sample. To quantify RNA, QPCR or real-time PCR is preceded by the step of reverse transcribing mRNA into cDNA. This is referred to herein as "real-time RT-PCR" or "quantitative RT-PCR" or "q RT-PCR".

The Taqman method of PCR product quantification uses a fluorescent reporter probe. This is more accurate since the probe is designed to be sequence-specific and will only bind to the specific PCR product. The probe specificity allows for quantification even in the presence of non-specific DNA amplification. This allows for multiplexing, which quantitates several genes in the same tube, by using probes with different emission spectra. Breakdown of the probe by the 5' to 3' exonuclease activity of Taq polymerase removes the quencher and allows the PCR product to be detected.

When plotted on a linear scale, the fluorescent emission increase with PCR cycle number has a sigmoidal shape with an exponential phase and a plateau phase. The plateau phase is determined by the amount of primer in the master mix rather than the nucleotide template. Usually the vertical scale is plotted in a logarithmic fashion, allowing the intersection of the plot with the threshold to be linear and more easily visualized. Theoretically, the amount of DNA doubles every cycle during the exponential phase, but this is affected by the efficiency of the primers used. A positive control using a reference gene, e.g., a "housekeeping" gene that is relatively abundant in all cell types, is also performed to allow for comparisons between samples. The amount of DNA/RNA is determined by comparing the results to a standard curve produced by serial dilutions of a known concentration of DNA/RNA.

The present disclosure includes a polynucleotide comprising: (i) a nucleic acid sequence of at least 90%, 91%, 92%, 93%, 94%, 95%, 96%, 97%, 98%, 99%, or 100% sequence identity, based on the Clustal V method of alignment, when compared to SEQ ID NO:1, SEQ ID NO:2, SEQ ID NO:3, SEQ ID NO:4, SEQ ID NO:5, SEQ ID NO:6, SEQ ID NO:7 or SEQ ID NO:24; or (ii) a nucleic acid sequence of at least 90%, 91%, 92%, 93%, 94%, 95%, 96%, 97%, 98%, 99% or 100% sequence identity, based on the Clustal V method of alignment, when compared to a functional fragment of SEQ ID NO:1, SEQ ID NO:2, SEQ ID NO:3, SEQ ID NO:4, SEQ ID NO:5, SEQ ID NO:6, SEQ ID NO:7 or SEQ ID NO:24; or (iii) a full complement of the nucleic acid sequence of (i) or (ii), wherein the polynucleotide acts as a terminator in a plant cell.

Embodiments of the Disclosure Include:

The present disclosure relates to terminator sequences. Recombinant DNA constructs comprising terminator sequences are provided.

An embodiment of this disclosure is an isolated polynucleotide sequence comprising (a) the sequence set forth in SEQ ID NOS: 1, 2, 3, 4, 5, 6, 7 or 24; (b) a sequence with at least 95% sequence identity to SEQ ID NOS: 1, 2, 3, 4, 5, 6, 7 or 24; or (c) a sequence comprising a functional fragment of (a) or (b), wherein the isolated polynucleotide sequence functions as a terminator in a plant cell and where the polynucleotide is operably linked to a heterologous polynucleotide. In another aspect, this disclosure concerns a recombinant DNA construct comprising a promoter, at least one heterologous nucleic acid fragment, and any terminator, or combination of terminator elements, of the present disclosure, wherein the promoter, at least one heterologous nucleic acid fragment, and terminator(s) are operably linked.

Recombinant DNA constructs can be constructed by operably linking the nucleic acid fragment of the disclosure, the terminator sequences set forth SEQ ID NOS: 1, 2, 3, 4, 5, 6, 7 or 24 or a functional fragment of the nucleotide sequence set forth in SEQ ID NOS: 1, 2, 3, 4, 5, 6, 7 or 24 to a heterologous nucleic acid fragment.

Another embodiment of this disclosure is a method of expressing a heterologous polynucleotide in a plant, comprising the steps of introducing into a regenerable plant cell the recombinant DNA construct described above and regenerating a transgenic plant from the transformed regenerable plant cell, wherein the transgenic plant comprises the recombinant DNA construct and exhibits expression of the heterologous polynucleotide.

Another embodiment of this disclosure is a method of expressing a heterologous polynucleotide in a plant, comprising the steps of introducing into a regenerable plant cell the recombinant DNA construct described above; regenerating a transgenic plant from the regenerable plant cell described above; and obtaining a progeny plant from the transgenic plant, wherein the transgenic plant and the progeny plant comprises the recombinant DNA construct and exhibits expression of the heterologous polynucleotide.

In another embodiment, this disclosure concerns a vector, cell, plant, or seed comprising a recombinant DNA construct comprising the terminator sequences described in the present disclosure.

The disclosure encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the terminator sequences described in the present disclosure is a monocotyledonous plant. In another embodiment, the plant comprising the terminator sequences described in the present disclosure is a maize plant.

EXAMPLES

The present disclosure is further illustrated in the following Examples, in which parts and percentages are by weight and degrees are Celsius, unless otherwise stated. It should be understood that these examples, while indicating embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1: Amplification and Cloning of a Terminator Sequence

Primers (SEQ ID NOS: 8 through 21) were designed for amplifying the terminators of selected genes from *Sorghum bicolor* (SAG, CPI, XSP, PMSP, CP, PSLP, SCI, PEPC) and *Oryza sativa* (UBI) based on the *Sorghum bicolor* and *Oryza sativa* genomic sequence database. The primer sequences are given in Table 3, the underlined region is not homologous with genomic template:

TABLE 3

| TERM | SEQ ID | Forward Primer Sequence | SEQ ID | Reverse Primer Sequence |
|---|---|---|---|---|
| SB-SAG12_TERM | 8 | TCTAGAGATCTGGTACCTCAGCCGTCAACAGCCAGGGTGA | 9 | AAGCTTCGGTCCGCTAACTAACTAGGCGTTGAACCGTTGATAGCA |
| SB-CPI8_TERM | 10 | TCTAGAGGATCCGGTACCGGCTCCACGTAGTCGTTATC | 11 | AAGCTTCGGTCCGCTAACTAACTAGTGCGGGGCGACGGATCACGG |
| OS-UBI_TERM | 12 | TCTAGAGGATCCAGCTGCTGCTGTTCTAGGGTTCAC | 13 | AAGCTTCGGTCCGCTAACTAACTAGGAAGCCTACCAAAGCAAAGC |
| SB-PMSP_TERM | 14 | TCTAGAGGATCCGGTACCCTAGAAGATGCTGTGACAGGC | 15 | AAGCTTCGGTCCGCTAACTAACTAGGCAGCTATGAATTATTTCAA |
| SB-CP1_TERM | 16 | TCTAGAGGATCCGGTACCACTCTGATCAGTTGTCTTCC | 17 | AAGCTTCGGTCCGCTAACTAACTAGTCAATCTTTCGTTCAGTACC |
| SB-SCI-1B_TERM | 18 | TCTAGAGGATCCGGTACCCCCATCAGGAAGGATGAAGCG | 19 | AAGCTTCGGTCCGCTAACTAACTAGCTGGCTGCTTATCAATTCCA |
| SB-PEPC1_TERM | 20 | TCTAGAGGATCCGGTACCCCGCCAGATCCTCGGTGTACAAATA | 21 | GATATCCGGTCCGCTAACTAACTAGTATGTTGCTTAGGCCTCTTT |

For example: SB-SAG12_TERM

SEQ ID NO: 8(forward primer):
TCTAGAGATCTGGTACCTCAGCCGTCAACAGCCAGGGTGA

SEQ ID NO: 9(reverse primer):
AAGCTTCGGTCCGCTAACTAACTAGGCGTTGAACCGTTGATAGCA

Figure 1:
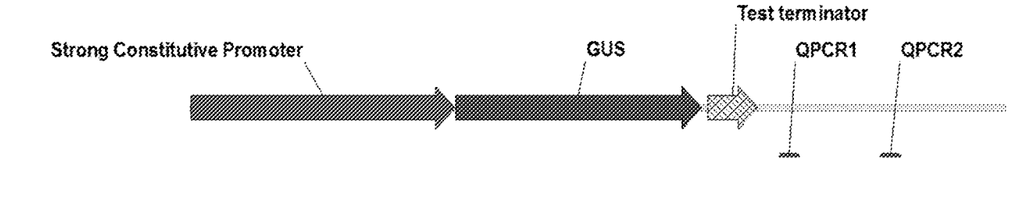
FIG. 1 Shows the configuration of the terminator testing cassette and positions of the QRT-PCR amplicons.

Each terminator (SEQ ID NO: 1-7) was amplified by PCR using these primers. The product was cloned into pGEM-T Easy vector (Promega, Cat #A1360) and the sequence was confirmed. Each terminator included about the predicted 3' UTR (size noted in Table 1) along with a portion of downstream sequence. The amplified sequence of each terminator (SEQ ID NO: 1-7), including control terminators PINII (SEQ ID NO: 22) and SB-GKAF (SEQ ID NO:23) were then cloned into an expression vector containing a terminator testing cassette shown in FIG. 1.

Example 2: Stable Transformation Assays to Test Terminator Activity

Quantitative Reverse Transcriptase-PCR (qRT-PCR) assays were done from leaf samples taken at the R1 developmental stage of stably transformed plant tissues grown in the greenhouse. The assays were designed to quantify the level of expression of the GUS transcript, and to test the ability of isolated terminator sequences (SEQ ID NO:1-7) to stop transcription (that is prevent read-through transcription).

GUS Expression Analysis:

Multiple plants were tested for each construct and each was analyzed for expression of the GUS gene. Table 4 shows the QTR-PCR results for GUS expression. Those results were normalized to the results for the PIN II TERM (SEQ ID NO: 22) and ranked 1-9 with 1 showing the highest expression.

TABLE 4

| Terminator | Ave. Ref CT | Ave. GUS CT | (Ave. GUS CT) − (Ave. Ref CT) | Average Expression Relative to PinII | GUS Expression Rank |
|---|---|---|---|---|---|
| SB-SAG12_TERM | 21.391 | 22.649 | 1.258 | 6.417 | 1 |
| SB-PEPC1_TERM | 22.369 | 24.24 | 1.871 | 4.196 | 2 |
| SB-CP1_TERM | 20.924 | 23.014 | 2.09 | 3.605 | 3 |
| SB-SCI-1B_TERM | 22.448 | 25.201 | 2.753 | 2.277 | 4 |
| OS-UBI_TERM | 21.036 | 23.982 | 2.945 | 1.993 | 5 |
| SB-CP18_TERM | 21.452 | 24.781 | 3.329 | 1.527 | 6 |
| SB-GKAF TERM | 21.098 | 25 | 3.902 | 1.027 | 7 |
| PINII TERM | 22.509 | 26.449 | 3.94 | 1.000 | 8 |
| SB-PMSP_TERM | 22.707 | 27.685 | 4.978 | 0.487 | 9 |

Quantitative Reverse Transcriptase PCR (qRT-PCR) to Determine Read-Through Transcription:

Samples from each plant were tested for the presence of read-through transcript. This is a transcript that has proceeded through the tested terminator. To assess presence of products that would indicate that transcription was continuing past the terminator, amplification was targeted downstream of the terminator being tested. Two primer sets were designed downstream of the tested terminators. Table 5 shows results of QRT-PCR testing for determination of transcription downstream of the test terminator. QPCR1 is the QRT-PCR target sequence 200 bp downstream of the terminator. QPCR2 is the QRT-PCR target sequence 700 bp downstream of the terminator. "Fully terminated" transcripts have no measured QRT-PCR expression at that amplicon. In Table 5, those are designated as QPCR1 and QPCR2. The QPCR1 target was ~200 nt from the terminator, and the QPCR2 target was ~500 nt from the terminator. Results are given as "% events fully terminated". This is the % of events that had no expression for the target amplicon (i.e. QPCR1 or QPCR2).

TABLE 5

| Terminator | TERM Length (bp) | % events fully terminated by QPCR1 position (~200 bp Downstream) | % events fully terminated by QPCR2 position (~700 bp downstream) |
|---|---|---|---|
| SB-SAG12_TERM | 980 | 100 | 100 |
| SB-PEPC1_TERM | 997 | 100 | 100 |
| SB-CP1_TERM | 989 | 100 | 100 |
| SB-SCI-1B_TERM | 953 | 80 | 80 |
| OS-UBI_TERM | 950 | 100 | 100 |
| SB-CPI8_TERM | 980 | 100 | 100 |
| SB-GKAF TERM | 462 | 100 | 100 |
| PINII TERM | 311 | 75 | 75 |
| SB-PMSP_TERM | 964 | 100 | 100 |

Example 3: Endogenous Gene Expression Modification Through Genome Editing

In an embodiment, the terminator elements set forth in SEQ ID NOS: 1-7 or 24 or fragments thereof, and compositions comprising said sequences, can be inserted in operable linkage with an endogenous gene by genome editing using a double-stranded break inducing agent, such as a guided Cas9 endonuclease. Based on the availability of the genetic loci sequence information guide RNAs are designed to target a particular endogenous gene. For example, maize genes involved in improving agronomic characteristics of a maize plant are suitable targets.

Guided Cas9 endonucleases are derived from CRISPR loci (Clustered Regularly Interspaced Short Palindromic Repeats) (also known as SPIDRs—SPacer Interspersed Direct Repeats) which are a family of recently described DNA loci. CRISPR loci are characterized by short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

Cas endonuclease relates to a Cas protein encoded by a Cas gene, wherein the Cas protein is capable of introducing a double strand break into a DNA target sequence. The Cas endonuclease is guided by a guide polynucleotide to recognize and optionally introduce a double strand break at a specific target site into the genome of a cell (U.S. Application Publication No. 2015/0082478). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

In one embodiment, the methods comprise modifying the expression of an endogenous gene in a cell by introducing the terminator elements herein in operable linkage with an endogenous gene. The terminator elements can be introduced in operable linkage to an endogenous gene using any genome editing technique, including, but not limited to use of a double-stranded break inducing agent, such as guided Cas9/CRISPR system, Zinc finger nucleases, TALENs. See Ma et al (2014), *Scientific Reports,* 4:4489; Daimon et al (2013), *Development, Growth, and Differentiation*, 56(1): 14-25; and Eggleston et al (2001) *BMC Genetics*, 2:11.

Example 4: SB-PEPC1_TERM (MOD1) (SEQ ID NO: 24)

SB-PEPC1_TERM (SEQ ID NO: 7) was modified to remove restriction sites. Five (5) single base pair changes were made to SB-PEPC1_TERM (SEQ ID NO: 7) to provide SB-PEPC1_TERM (MOD1) (SEQ ID NO: 24), which has 99.5% sequence identity to SB-PEPC1_TERM (SEQ ID NO: 7). SB-PEPC1_TERM (MOD1) (SEQ ID NO: 24) was used in multiple constructs and did not alter the expected expression patterns of the genes preceding SB-PEPC1_TERM (SEQ ID NO: 7) (data not shown).

What is claimed is:

1. A recombinant DNA construct comprising SEQ ID NO: 3 wherein SEQ ID NO: 3 functions as a transcriptional terminator in a plant cell, and is operably linked to a heterologous polynucleotide sequence.

2. The recombinant DNA construct of claim 1, further comprising a promoter operably linked to the heterologous polynucleotide sequence.

3. A plant comprising the recombinant DNA construct of claim 1.

4. The plant of claim 3, wherein the plant is a monocot.

5. The plant of claim 3, wherein the plant is a maize plant.

6. A seed comprising the recombinant DNA construct of claim 1.

7. The seed of claim 6, wherein the seed is from a monocot plant.

8. The seed of claim 6, wherein the seed is from a maize plant.

9. A method of transforming a plant, comprising the steps of:
(a) introducing into a regenerable plant cell the recombinant DNA construct of claim 2;
(b) regenerating a transgenic plant from the regenerable plant cell of step (a), wherein the transgenic plant comprises the recombinant DNA construct of claim 2; and
(c) obtaining a progeny plant from the transgenic plant of step (b), wherein the progeny plant comprises the recombinant DNA construct of claim 2 and exhibits expression of the heterologous polynucleotide sequence.

10. The method of claim 9, wherein the plant is a monocot plant.

11. The method of claim 9, wherein the plant is a maize plant.

12. A plant stably transformed with a recombinant DNA construct comprising a terminator element of SEQ ID NO: 3 operably linked to a heterologous nucleic acid in the genome of the plant.

13. A method of modifying the expression of an endogenous gene of a plant, the method comprising introducing a terminator element of SEQ ID NO: 3 such that the introduced terminator element is operably linked to the endogenous gene to modify the expression of the endogenous gene.

14. The method of claim 13, wherein the terminator element is introduced through genome editing.

15. The method of claim 14, wherein the genome editing is performed through guided Cas9 endonuclease.

16. A plant comprising the recombinant DNA construct of claim 2.

17. A seed comprising the recombinant DNA construct of claim 2.

18. A method of transforming a plant, comprising the steps of:
(a) introducing into a regenerable plant cell the recombinant DNA construct of claim 2; and
(b) regenerating a transgenic plant from the regenerable plant cell of step (a), wherein the transgenic plant comprises the recombinant DNA construct of claim 2.

19. The plant of claim 16, wherein the plant is a monocot.

20. The plant of claim 16, wherein the plant is a maize plant.

21. The seed of claim 17, wherein the seed is from a monocot plant.

22. The seed of claim 17, wherein the seed is from a maize plant.

* * * * *

SEQUENCE LISTING

```
<160> NUMBER OF SEQ ID NOS: 24

<210> SEQ ID NO 1
<211> LENGTH: 980
<212> TYPE: DNA
<213> ORGANISM: Sorghum bicolor

<400> SEQUENCE: 1
gccgtcaaca gccagggtga ttagagcccc agcatgcaaa atgatcacct ggtcgctcat    60
ccttgactaa agcatggctc ggcggtcgct gtttacctat atccctatag taggtactcc   120
tgtacataaa gcctgaaaaa atgggttcag ttgtttatcg aactctgcca aatttgcttt   180
tgcatataat gtaaaattca gctagctctg ctaagctcct cgcttcagtt cgacagaact   240
gcaattgata ttgatgttat ggaaattgat attggaacaa tcagcaatat tatgcttata   300
ttcatttctt gggcgtgctc tactctgtgc cgatgatatc atccgatggg ttttgtactt   360
cttacttatg aagtgaacga taataggttg cctggtccca gttctcagct tgatgttatg   420
ataatcatat gtgatttcag ttctttgtct ggcattggtc tgtttttgtg tctgtgtctg   480
tgggctgtgg ctctgtgtgt tgataactcg agcttgattg catcagtgaa ctgcgactta   540
caacagcaga cagagtgtta gcagcaggga aggagaataa agaaattagg gagtaaagag   600
aacatagttg cctttcagag gacagcttag caagataaca aaattatgtt ctctccttt    660 aaggattaca gaggcatagc ctcagcgacg cgcgtgctag cggatccagt tatcatcatc   720
gtgttgggct tcctgggcct ggcctgccta gcaggcctgt cgacagcttc agaagggaa    780 ctcgttggcg gattgtccac agtagcacgt actatatgca gaaaaagtcc ttatgtctct   840
cttatcatta gcctattaat catattaatt cagtccacat aggaccgaat ttataactta   900
acaatctttt agtttcctga gcaatatcgt taaatcaaaa catattcttg taccaaattt   960
tgctatcaac ggttcaacgc                                               980

<210> SEQ ID NO 2
<211> LENGTH: 980
<212> TYPE: DNA
<213> ORGANISM: Sorghum bicolor

<400> SEQUENCE: 2
ggctccacgt agtcgttatc gacgatcggc gacactactg gagttggagc aacgtctagt    60
tccagcaata atataatgca atattactgt agtagtagta gtatactata ggacccctcc   120
tagctagcat gcggacatgc tcttgtgatc ttgtctcggg tccagacttc aataaagcca   180
tcttggcatt atatgtacta tacaaaaaag attatcactg ctttctctcg atcgcaaatc   240
atcctgtttt ttttttggc aaaaagttca gcgtttcttt ctctctctct gactaccaaa    300
ctgttgacag aaagaaaaag gtcaaggag tttgcgtacg tacagtacag acataaaaaa    360
acaaacacaa gcagaaatat caaatactgt gtttggttgt tgtggcacgt tgggcgtggt   420
ggaactgcgg cacagttctt cgtgtagttt tgcacaactt ctgcctaaag ttcgcactga   480
```

| | |
|---|---|
| tttcttgcac tagatattcg gggacaccac agctacctgc gcgcgtataa ggtaaacagg | 540 |
| ccctaataac aaccgtctca atattgtgtg atgtgtttga ggtcagattt gatcaatcaa | 600 |
| gaacatctta acctataaga tataggtaaa taacaagcca tctctttaac agtgaacatg | 660 |
| tgtctctcaa acatattaaa taatattggt gcggttagtg tgaagaaagt actgttagct | 720 |
| gatttgttgt gaaagaaaaa tattactgaa tgactaacat ctcttccaaa ctaaatgttt | 780 |
| gcgtgtgaaa taatggatat tgtcggttcc aaactaaatg tttgcgtgtg aaataatgga | 840 |
| tattgtcgga tagagcacaa ggtgctcagc ttctgcaccc aatataattt cactcaagaa | 900 |
| cgagcaggat atcgatcgac gatctcaaat gagcaacacg agctcagcat aatatcgtga | 960 |
| gccgtgatcc gtcgccccgc | 980 |

<210> SEQ ID NO 3
<211> LENGTH: 950
<212> TYPE: DNA
<213> ORGANISM: Oryza sativa

<400> SEQUENCE: 3

| | |
|---|---|
| agctgctgct gttctagggt tcacaagtct gcctatttgt cttccccaat ggagctatgg | 60 |
| ttgtctggtc tggtccttgg tcgtgtcccg tttcattgtg tactatttac ctgtaatgtg | 120 |
| tatccttaag tctggtttga tggtgtctga aacgttttgc tgtggtagag cagcatggaa | 180 |
| gaactataat gaataagtga tccctaatca ttgtgtccaa attttgcttc tgctataccc | 240 |
| ttttgtgctg tttcttatgt tttgcttaaa aatttgatct gacaaacaaa tttgtctaaa | 300 |
| ttatgctctt gttctgactg tgtactgtac acatttgtat tgctaccggt ttggcacata | 360 |
| gttttctctt tgattgcaga tcaaacccct ctgattgcag attgcttggc tatggctgat | 420 |
| gtgctcactg ttcttcttta gcttgtatat tgctgatggt ggcttggcta cggctgaaaa | 480 |
| agttgctgct gcgccgactt ggcaactgtt gctccagtaa tgctttgtcc tctcttccta | 540 |
| gccgccgact tggcacttgg cagctgttgc tcctgtaatg cgttgttatc tcttatctct | 600 |
| tgagatgtac tatgattttg aggctgtttg acttgtgcca gattgccagt gctgatgcta | 660 |
| tattatctca ggttttttatg ctagtatatg ttttactgtg tgctgcctgt gtcgagttac | 720 |
| gtaatctatt gaaccgctat gcgtgttgat gccctgttgt tgcttgccag attgatgccc | 780 |
| ctgttgcttg cagcttgcaa gctgtagtga atcctaaaaa ttcgaaacca aatctattct | 840 |
| gaacttttga agatctgtga tgtccggaag aaaagattca aacagataaa cgggactctc | 900 |
| cagaatctat aaaataaatg atcgacaaac gctttgcttt ggtaggcttc | 950 |

<210> SEQ ID NO 4
<211> LENGTH: 964
<212> TYPE: DNA
<213> ORGANISM: Sorghum bicolor

<400> SEQUENCE: 4

| | |
|---|---|
| tagaagatgc tgtgacaggc gctagagagt agagaatagg agagcgagtt gtggctctga | 60 |
| aatccgaggc cttgagctgc agaggaatgc tgtaattttt tcatagcctg tagagaataa | 120 |
| gagttagcac agtgctgtac ctgtacgtgt tatgcatgcc ctccaggttg taaaatatat | 180 |
| atttgggtgt ttaagcctat gtgacatgat gaccagagtc cagagagggc atccctcctc | 240 |
| taatgcatgg aaatttgaat ctcatctgga ttatttctgt gtgttccatt cagagttttt | 300 |
| cttacattag gctggaacct taaccataaa actccccaaa tctaagcaac gaaaataaaa | 360 |
| tgtgtgaaat ttatttttcaa gatggcacaa attctgggat gtggggagga tgcaataacc | 420 |

| | |
|---|---|
| ctttttttttt agggaggat gcaaaaaaga aaaaactcta ttttcctct cccaaatttt | 480 |
| acgaaagtct gcttttcctt cctcaatttc aaaccaggc aaaccacctc tctcaactt | 540 |
| tcaaaccgtg cattttacct ctctaaagcg gttttgctat agtgacggtg attttgtctt | 600 |
| ttttaattat tccgactaaa atctttgaaa atcatagta aatcacagaa aaatcataaa | 660 |
| atagaaatct aatttttga actccacata agtagatcta cataataaac ataataata | 720 |
| gtatgcttta gtacaaagtt ttttataaag gttttgtctt tttcttttt atttatttcg | 780 |
| actaaatatt tgaaaaatca tagtaaatta cagaaaaatc ataaaatata aaatctaatt | 840 |
| ttgtagcctc cacatgagca tatctacaca gtaaatatgt aatatggtat gctttagtat | 900 |
| aatttttta ttgtagcttt tgatctacgt ttttctgtaa ttaattgaaa taattcatag | 960 |
| ctgc | 964 |

<210> SEQ ID NO 5
<211> LENGTH: 989
<212> TYPE: DNA
<213> ORGANISM: Sorghum bicolor

<400> SEQUENCE: 5

| | |
|---|---|
| actctgatca gttgtcttcc ctgattataa tggtgatttc atatattgta gaactacaat | 60 |
| tcctgccagt aatatatgct ccatctgtgc tgttttatat atcgaaggca gcaaagatgt | 120 |
| gaagcggcaa cgcgatgctt gctgtaagtt tatgtttggc ttgcgacgaa tgctacacgc | 180 |
| tatttggatg tagcaaagtt atcaacatct gtatacgcat tttaatctac aaaacttttg | 240 |
| aataatttgt acataaaatt atggtgtgct tccatctttg ctatatgtgt ttgatgtgct | 300 |
| tatgggtttt ggtctgtagc ttgcgtaacc tgattgggaa acaaacaaac aggcgagacc | 360 |
| gataaatcct aaggcctagt tcactaaaaa acttttcaag attcttggtc atatcgaatc | 420 |
| ttgtggcaca tgcatggagt actaaatata gatgaaaata aaaactaatt gtacagttta | 480 |
| cctgtaaatc gcgagataaa tctttttaagc ctagttactc tatgattgta cgatgtttgt | 540 |
| taaataaaaa caaaaatgct acggttccga aaaccaaaaa aaaattagag caaacacatc | 600 |
| tatatctata aatcttatag taacaatgag agctcagagc cgaacttagg ccttgttcgt | 660 |
| aaaaatttc aagattttcc gtcacatcga atctttggtc tcatacatgg agcattaaat | 720 |
| aaagataaaa ataaaaacta attacacagt ttatctgaaa tttgtgaaat gaatcttttg | 780 |
| agcctagtta ctccgtgatt ggacaatgtt tgtcaaataa aaacaaaagt gctacagtag | 840 |
| ccaaaaaaac caaatttta cgaactaaac aaggccttat aataaagtgg aattggaagc | 900 |
| tcgggcatag ttatcagaga ttcaggcggg cgattcatcg ctgcatcaat gatttgtttt | 960 |
| tttgcctgtg gtactgaacg aaagattga | 989 |

<210> SEQ ID NO 6
<211> LENGTH: 953
<212> TYPE: DNA
<213> ORGANISM: Sorghum bicolor

<400> SEQUENCE: 6

| | |
|---|---|
| ccatcaggaa ggatgaagcg cccctcattt tgtgccctag gtcgtggatt gctggatttt | 60 |
| aattttacac atttccttgt cgatcctttc tgctgtgtgt ggttcgagaa tgttagtgtg | 120 |
| ttatcgcaag atctgggtgt ttggaagtta tctcattatt gggcctcata aattcataat | 180 |
| tcttgccagt tagtgacaac tgtagcttag gtttacttct gcttgtagta catcgcctag | 240 |

```
atcgtgggag tccctctttt cagacgaatg tcatgaaaca ttggttttg gaaatgatta      300
ggaagacatt tgctgttttg tcgactgctg ttttttacgg ccaagttcag agttttttt      360
ttcatgtaca aagtatcagc agttaaatta tgttaccttt accatggttc ttcatatttg    420
ttttccttcc attgctcaat ctatgtcatc ttttgaaatg gtttggaagg catcctttat    480
aggatatata gatatagatt tgaagcataa ttgttaggat aagacaccag ctagcctatg    540
ctgcaacgca cattattcga cccttaataa caacaggtga tttttatatt ataaaaaagt    600
tggaaaagta tacacaagaa ttttcaaaa gaagggtaaa agggaacagc cctcctgctc      660
gacaattgga attggtgtcc cgcataattt ttttctgcct ttgagaattc aggcgtctct    720
ggattctagt tcaccattta ccaattagaa ggaatactat gtatgtataa ttctacaatc    780
tgcattctac acaatccttc tattttctga atatagttgc aagactaggg ctctcttata    840
gtatttctaa ttatagccgc tttgcaaagt actgtcatat ttgattaggg gtattggaaa    900
gaaggagaaa agggtgacac cctgcttgac aattggaatt gataagcagc cag           953
```

```
<210> SEQ ID NO 7
<211> LENGTH: 997
<212> TYPE: DNA
<213> ORGANISM: Sorghum bicolor

<400> SEQUENCE: 7
```

```
gccagatcct cggtgtacaa ataaccccgtc ttatcctatg agacgggccg gcgtcagtgt     60
gttctggagg aattttatg tcagagcctt tttctttgtg tgcttgatgt agatgccaag     120
ggaagcttat tggctgttga agcttgatgc aaaataaatt atggaactct gttttttgtt   180
tatctaataa taactagcaa atatgcttcc attgcattga aactaacagc cttttgtgtt    240
tccaagtttt attttgtgac aatgtcatct atttcaatta gttgtggaat cggaaacttg    300
caggtctaac ttggaaactc caatccctca ggatcctgga cttttcctg gtgtaatcca    360
tgtagatatt attttaatca tcattttagt tctggaggtt ttccatctc cggttttgct    420
cccctttctt caaaaaaaaa aaaaaatgc cgtaggcgcc gcaacgccca cctgttgttc     480
aaactcatgg gcacgagtgg ctcgaagatt ttatacaaca attgctgtag tttcaccgtt    540
gctggtgaag aagcattttt ttaaaaaaat atagtggtat tcatttaat tagtttagtt    600
gtgcagcgag caaatttgg acatgctctg ctcggaatct gatcgaccta gacacagatt    660
agcagcagta gctttgtcat ctgttccaag agttgcgatc tgatagaaga aaaaaaaacc    720
ttcccttcaa tgtaaaaccg aaactaacaa gaaagaagca cagtgccgtt taggcaagta    780
tggagtacgt attaagcatg tagatggcca tgcatgaacc actaacaaga aagaagcgca    840
gtgccattca gcaagcata agcatgtaga ttggcatgca tgaacaacta acagtagatg     900
gtctctggtc tgattagaag ttttttggga agccaagaaa acatgtacaa ctggttccat    960
ctcaaattcc gtggcaaaaa gaggcctaag caacata                              997
```

```
<210> SEQ ID NO 8
<211> LENGTH: 40
<212> TYPE: DNA
<213> ORGANISM: Artificial sequence
<220> FEATURE:
<223> OTHER INFORMATION: primer

<400> SEQUENCE: 8
```

```
tctagagatc tggtacctca gccgtcaaca gccagggtga                            40
```

<210> SEQ ID NO 9
<211> LENGTH: 45
<212> TYPE: DNA
<213> ORGANISM: Artificial sequence
<220> FEATURE:
<223> OTHER INFORMATION: primer

<400> SEQUENCE: 9
aagcttcggt ccgctaacta actaggcgtt gaaccgttga tagca            45

<210> SEQ ID NO 10
<211> LENGTH: 38
<212> TYPE: DNA
<213> ORGANISM: Artificial sequence
<220> FEATURE:
<223> OTHER INFORMATION: primer

<400> SEQUENCE: 10
tctagaggat ccggtaccgg ctccacgtag tcgttatc                     38

<210> SEQ ID NO 11
<211> LENGTH: 45
<212> TYPE: DNA
<213> ORGANISM: Artificial sequence
<220> FEATURE:
<223> OTHER INFORMATION: primer

<400> SEQUENCE: 11
aagcttcggt ccgctaacta actagtgcgg ggcgacggat cacgg             45

<210> SEQ ID NO 12
<211> LENGTH: 36
<212> TYPE: DNA
<213> ORGANISM: Artificial sequence
<220> FEATURE:
<223> OTHER INFORMATION: primer

<400> SEQUENCE: 12
tctagaggat ccagctgctg ctgttctagg gttcac                       36

<210> SEQ ID NO 13
<211> LENGTH: 45
<212> TYPE: DNA
<213> ORGANISM: Artificial sequence
<220> FEATURE:
<223> OTHER INFORMATION: primer

<400> SEQUENCE: 13
aagcttcggt ccgctaacta actaggaagc ctaccaaagc aaagc             45

<210> SEQ ID NO 14
<211> LENGTH: 39
<212> TYPE: DNA
<213> ORGANISM: Artificial sequence
<220> FEATURE:
<223> OTHER INFORMATION: primer

<400> SEQUENCE: 14
tctagaggat ccggtaccct agaagatgct gtgacaggc                    39

<210> SEQ ID NO 15
<211> LENGTH: 45
<212> TYPE: DNA
<213> ORGANISM: Artificial sequence
<220> FEATURE:
<223> OTHER INFORMATION: primer

<400> SEQUENCE: 15
aagcttcggt ccgctaacta actaggcagc tatgaattat ttcaa                45

<210> SEQ ID NO 16
<211> LENGTH: 38
<212> TYPE: DNA
<213> ORGANISM: Artificial sequence
<220> FEATURE:
<223> OTHER INFORMATION: primer

<400> SEQUENCE: 16
tctagaggat ccggtaccac tctgatcagt tgtcttcc                         38

<210> SEQ ID NO 17
<211> LENGTH: 45
<212> TYPE: DNA
<213> ORGANISM: Artificial sequence
<220> FEATURE:
<223> OTHER INFORMATION: primer

<400> SEQUENCE: 17
aagcttcggt ccgctaacta actagtcaat ctttcgttca gtacc                 45

<210> SEQ ID NO 18
<211> LENGTH: 38
<212> TYPE: DNA
<213> ORGANISM: Artificial sequence
<220> FEATURE:
<223> OTHER INFORMATION: primer

<400> SEQUENCE: 18
tctagaggat ccggtacccc atcaggaagg atgaagcg                         38

<210> SEQ ID NO 19
<211> LENGTH: 45
<212> TYPE: DNA
<213> ORGANISM: Artificial sequence
<220> FEATURE:
<223> OTHER INFORMATION: primer

<400> SEQUENCE: 19
aagcttcggt ccgctaacta actagctggc tgcttatcaa ttcca                 45

<210> SEQ ID NO 20
<211> LENGTH: 42
<212> TYPE: DNA
<213> ORGANISM: Artificial sequence
<220> FEATURE:
<223> OTHER INFORMATION: primer

<400> SEQUENCE: 20
tctagaggat ccggtacccg ccagatcctc ggtgtacaaa ta                    42

<210> SEQ ID NO 21
<211> LENGTH: 45
<212> TYPE: DNA
<213> ORGANISM: Artificial sequence
<220> FEATURE:
<223> OTHER INFORMATION: primer

<400> SEQUENCE: 21
gatatccggt ccgctaacta actagtatgt tgcttaggcc tcttt                 45

<210> SEQ ID NO 22
<211> LENGTH: 311

```
<212> TYPE: DNA
<213> ORGANISM: Solanum tuberosum

<400> SEQUENCE: 22
cctagacttg tccatcttct ggattggcca acttaattaa tgtatgaaat aaaaggatgc    60
acacatagtg acatgctaat cactataatg tgggcatcaa agttgtgtgt tatgtgtaat   120
tactagttat ctgaataaaa gagaaagaga tcatccatat ttcttatcct aaatgaatgt   180
cacgtgtctt tataattctt tgatgaacca gatgcatttc attaaccaaa tccatataca   240
tataaatatt aatcatatat aattaatatc aattgggtta gcaaaacaaa tctagtctag   300
gtgtgttttg c                                                        311

<210> SEQ ID NO 23
<211> LENGTH: 462
<212> TYPE: DNA
<213> ORGANISM: Sorghum bicolor

<400> SEQUENCE: 23
actaactatc tatactgtaa taatgttgta tagccgccgg atagctagct agtttagtca    60
ttcagcggcg atgggtaata ataaagtgtc atccatccat caccatgggt ggcaacgtga   120
gcaatgacct gattgaacaa attgaaatga aagaagaaa tatgttatat gtcaacgaga   180
tttcctcata atgccactga cgacgtgtgt ccaagaaatg tatcagtgat acgtatattc   240
acaatttttt tatgacttat actcacaatt tgttttttta ctacttatac tcacaatttg   300
ttgtgggtac cataacaatt tcgatcgaat atatatcaga aagttgacga agtaagctc   360 actcaaaaag ttaaatgggc tgcggaagct gcgtcaggcc caagttttgg ctattctatc   420
cggtatccac gattttgatg gctgagggac atatgttcgc tt                      462

<210> SEQ ID NO 24
<211> LENGTH: 997
<212> TYPE: DNA
<213> ORGANISM: Sorghum bicolor
<220> FEATURE:
<221> NAME/KEY: terminator
<222> LOCATION: (1)..(997)

<400> SEQUENCE: 24
gccagatcct cggtgtacaa ataacccgtc ttatcctatg agacgggccg gcgtcagtgt    60
gttctggagg aattttttatg tcagagcctt tttctttgtg tgcttgatgt agatgccaag   120
ggaagcttat tggctgttga agcttgatgc aaaataaatt atggaactct gttttttgtt   180
tatctaataa taactagcaa atatgcttcc attgcattga aactaacagc cttttgtgtt   240
tccaagtttt attttgtgac aatgtcatct atttcaatta gttgtggaat cggaaacttg   300
caggactaac ttggaaactc caatccctca gcatcctgga cttttcctg gtgtaatcca   360 tgtagatatt atttttaatca tcattttagt tctggaggtt tttccatctc cggttttgct   420
cccctttctt caaaaaaaaa aaaaaaatgc cgtaggcgcc gcaacgccca cctgttgttc   480
aaactcatgg gcacgagtgg ctcgaagatt ttatacaaca attgctgtag tttcaccgtt   540
gctggtgaag aagcattttt ttaaaaaaat atagtggtat tcatttaat tagtttagtt   600 gtgcagcgag caaaatttgg acatgctctg ctcggaatct gatcgaccta gacacagatt   660
agcagcagta gctttgtcat ctgttccaag agttgcgatc tgatagaaga aaaaaaaacc   720
ttcccttcaa tgtaaaaccg aaactaacaa gaaagaagca cagtgccgtt taggcaagta   780
tggagtacgt attaagcatg tagaaggcca tgcatgaacc actaacaaga aagaagcgca   840
```

```
gtgccattca ggcaagcata agcatgtaga ttggcatgca tgaacaacta acagtagatc    900
gtctctggtc tgattagaag tttttggga  agccaagaaa tcatgtacaa ctggttccat    960
ctcaaattcc gtggcaaaaa gaggcctaag caacata                             997
```